US012788980B2

(12) United States Patent
Krieg et al.

(10) Patent No.: US 12,788,980 B2
(45) Date of Patent: Nov. 10, 2026

(54) NANOSECOND PULSED ELECTRIC FIELD SYSTEM

(71) Applicant: Pulse Biosciences, Inc., Hayward, CA (US)

(72) Inventors: Kenneth R. Krieg, Fremont, CA (US); Gregory P. Schaadt, Santa Clara, CA (US); Chaofeng Huang, San Jose, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 150 days.

(21) Appl. No.: 18/415,612

(22) Filed: Jan. 17, 2024

(65) Prior Publication Data

US 2024/0149062 A1 May 9, 2024

Related U.S. Application Data

(62) Division of application No. 16/940,381, filed on Jul. 27, 2020, now Pat. No. 11,904,164.

(51) Int. Cl.
*A61N 1/36* (2006.01)
*G06F 21/44* (2013.01)

(52) U.S. Cl.
CPC ....... *A61N 1/36034* (2017.08); *A61N 1/3603* (2017.08); *G06F 21/44* (2013.01)

(58) Field of Classification Search
CPC .............. A61N 1/3603; A61N 1/36034; A61B 18/1233; A61B 2018/00178
See application file for complete search history.

(56) References Cited

U.S. PATENT DOCUMENTS

| | | | | |
|---|---|---|---|---|
| 6,326,177 | B1 | 12/2001 | Schoenbach et al. | |
| 8,000,813 | B2 | 8/2011 | Schoenbach et al. | |
| 8,512,334 | B2 | 8/2013 | Nuccitelli et al. | |
| 8,822,222 | B2 | 9/2014 | Beebe et al. | |
| 9,101,764 | B2 | 8/2015 | Nuccitelli et al. | |
| 9,724,155 | B2 | 8/2017 | Nuccitelli et al. | |
| 10,850,095 | B2 | 12/2020 | Ebbers et al. | |
| 11,167,125 | B2 | 11/2021 | Moss et al. | |
| 11,904,164 | B2 * | 2/2024 | Krieg | A61N 1/36034 |

(Continued)

FOREIGN PATENT DOCUMENTS

WO WO2022/026359 A1 2/2022

OTHER PUBLICATIONS

Turovskiy et al.; U.S. Appl. No. 18/423,280 entitled "Multi-strut ablation and sensing catheter devices and methods," filed Jan. 25, 2024.

*Primary Examiner* — Eric D. Bertram
(74) *Attorney, Agent, or Firm* — Shay Glenn LLP

(57) ABSTRACT

Described herein are apparatuses (e.g., systems and devices) and methods of delivering nanosecond pulsed electrical fields (nsPEF). In particular, these apparatuses and methods may provide enhanced safety and robust operation over even very short (e.g., nanosecond and sub-nanosecond pulses) and high voltage pulsing; these benefits may be accomplished by multi-functional isolation of various subsystems and components of the apparatus, even including the low-voltage, control and command portions of the apparatus with extremely low capacitance, high voltage isolation.

21 Claims, 4 Drawing Sheets

(56) References Cited

U.S. PATENT DOCUMENTS

| | | | | |
|---|---|---|---|---|
| 2010/0000780 | A1* | 1/2010 | Zhu .................... | H01B 11/1895<br>174/350 |
| 2011/0092973 | A1 | 4/2011 | Nuccitelli et al. | |
| 2012/0078139 | A1* | 3/2012 | Aldridge ............ | A61B 18/1206<br>601/2 |
| 2014/0249522 | A1* | 9/2014 | Adanny ............. | A61B 18/1233<br>606/34 |
| 2014/0364797 | A1 | 12/2014 | Schoenbach et al. | |
| 2015/0187465 | A1* | 7/2015 | McErlean .............. | H01R 43/00<br>29/857 |
| 2015/0201991 | A1 | 7/2015 | Zemlin | |
| 2017/0245928 | A1 | 8/2017 | Xiao et al. | |
| 2017/0319851 | A1* | 11/2017 | Athos .................... | G01R 27/26 |
| 2018/0078755 | A1 | 3/2018 | Kreis et al. | |
| 2019/0274719 | A1* | 9/2019 | Stulen ...................... | A61B 8/56 |

* cited by examiner

NANOSECOND PULSED ELECTRIC FIELD SYSTEM

CROSS REFERENCE TO RELATED APPLICATIONS

This application is a division of U.S. patent application Ser. No. 16/940,381, filed Jul. 27, 2020, titled "NANOSECOND PULSED ELECTRIC FIELD SYSTEM," now U.S. Pat. No. 11,904,164, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses (systems and devices) described herein generally relate to rapid (e.g., nanosecond, picosecond, etc.) pulsing. In particular, described herein are nanosecond pulsing systems and apparatuses including hand-held applicators that may safely deliver high-voltage, nanosecond pulsed electrical fields (nsPEF) for electrotherapy.

BACKGROUND

A "nanosecond pulsed electric field" (nsPEF) may be applied for medical and/or therapeutic purposes, including in particular for the treatment of biological cells and tissues. NsPEF may include an electrical field with a sub-microsecond pulse width that may be less than about 1000 nanosecond (ns), such as between about 0.1 ns and 1000 ns, and may have peak voltages that are a relatively high voltage, in some variations as high as about 5 kV/cm (or greater), about 10 kV/cm (or greater), about 20 kV/cm (or greater), about 50 kV/cm (or greater), about 100 kV/cm (or greater), about 250 kV/cm (or greater), or about 500 kV/cm or greater. Such high voltage, very brief pulses present unique problems for therapeutic medical devices. In particular, the delivery of rapidly changing (e.g., nanosecond or faster) pulses at high voltage may result in induced currents in portions of the generator and applicator (e.g., handle, tip, cabling, etc.), including the low-voltage control circuitry portions, that may damage the circuitry.

The apparatuses and methods described herein may address the deficiencies of the prior art discussed above and may generally provide improvements over existing apparatuses and methods for generating, controlling and applying nanosecond pulsed electrical fields for medical and/or therapeutic purposes.

SUMMARY OF THE DISCLOSURE

Described herein are apparatuses, including systems and devices for nanosecond pulsed electrical field (nsPEF) generation and delivery, that are configured to allow the generation and delivery of variable-duration, nanosecond pulsed electrical fields for electrotherapy, including at pulse rates ranging from 0.1 per second (Hz) to 10,000 Hz or more. Such apparatuses and methods find particular use in the growing field of therapeutic nsPEF, including for the treatment of cancer/tumors, skin disorders and other applications.

In general, the apparatuses (e.g., systems and devices) and methods of delivering nanosecond pulsed electrical fields (nsPEF) described herein may provide for safe operation of even extremely fast (picosecond, nanosecond, etc.) pulse generators providing high voltages (e.g., up to at least about 5 kV/cm (or greater), at least about 10 kV/cm (or greater), at least about 20 kV/cm (or greater), at least about 50 kV/cm (or greater), at least about 100 kV/cm (or greater), at least about 250 kV/cm (or greater), or at least about 500 kV/cm or greater).

It may be difficult to provide very fast, e.g., brief, pulses at a therapeutic voltage without excess pulse generator output at non-therapeutic voltages, which may result in undesirable unwanted thermal effects. Generally, the faster the rise (and fall) time for a high voltage pulse, the more time the signal may be dwelling at the therapeutic voltage (e.g., the high voltage) rather than at the lower voltages that may result in non-therapeutic thermal effects. Thus, it is often desirable for the edges of rapid pulses to be very sharp, having a rise time that is very fast (e.g., about 150 ns or less, about 100 ns or less, about 50 ns or less, about 25 ns or less, about 20 ns or less, about 10 ns or less, etc.), such as a rise time of 20 ns or less from the output of a pulse generator of the apparatus. In one example, a tunable, high-voltage, nanosecond pulse generator may be based on a Marx topology hybrid circuit, having a plurality of different stages that each include at least one or a stack of power MOSFETs that allow relatively low charging voltages at each stage, while providing an overall higher generator output voltage with a single trigger. For example, see U.S. Application Ser. No. 15/148,334 (publication no. US20170245928A1, titled "High-voltage analog circuit pulser with feedback control"), herein incorporated by reference in its entirety.

The methods and apparatuses described herein for delivering high voltage, nanosecond pulses may include an applicator, which may be configured as a handle, that is connected by a cable to a controller and nanosecond pulse generator; the handle may include circuitry operating a low voltage but the same applicator may also deliver the high voltage, nanosecond pulsing. One or more safety features, including robust electrical isolation, may be included to protect both the apparatus and the user. For example, the apparatus may include multi-functional isolation within the pulse generator, as well as multi-functional isolation between the applicator, such as a handpiece (e.g., delivery tool), a delivery cable connecting the handpiece to the pulse generator, and the pulse generator. The multi-functional isolation prevents contact between the isolation zones of the apparatus that exceeds traditional AC isolation (low-frequency isolation). The multi-functional isolation may be referred to as a multi-functional isolation connection, as it may be determined between two (or more) regions or components.

The apparatuses and methods of using them described herein may be configured with one or more features that may provide multi-functional electrical isolation within the apparatus, protecting it from damage and operational instability, without substantially impacting system performance. Multi-functional electrical isolation may also be referred to herein as broadband galvanic isolation. Multi-functional isolation protects the apparatus, including component parts of the apparatus, during exposure to high voltage pulsed operation, providing very low capacitance between the components or subsystems. This multi-functional isolation provides electrical isolation for user, patient and subsystems by isolating against very low frequency (e.g., DC pathways), and also higher frequencies (e.g., up to 100-200 MHz or higher frequencies) present during pulsed operation.

Any of the methods and apparatuses described herein may include multi-functional isolation of the various components, to provide electrical isolation when using high voltage pulse outputs, such as when providing nanosecond or sub-nanosecond electrical stimulation, with low capacitance coupling between the components. Although nanosecond and sub-nanosecond stimulation my result in rapid voltage rise/fall times and potentially high currents across normal isolation barriers present in medical equipment, the multi-functional isolation described herein may protect these apparatuses as well as the patient's and user operating them. Multi-functional isolation may include very high common-mode transient immunity, high dielectric breakdown, and extremely low isolation capacitance. For example, a very high common mode transient immunity may provide protection beyond merely galvanic isolation at higher voltages. Multi-functional isolation may include isolation providing a high dielectric breakdown, which may refer to a dielectric breakdown in excess of, e.g., 5.7 kV (e.g., 5.7 kV or more, 6 kV or more, 7 kV or more, 8 kV or more, 9 kV or more, 10 kV or more, between 8-10 kV or more, etc.). The multi-functional isolation may include extremely low isolation capacitance, as mentioned above. Displacement current due to a voltage through a capacitance is the value of the capacitance times the rate of rise of the voltage. In the nanosecond (or sub-nanosecond) pulse generating systems described herein, the voltages in the system, including delivered to or output from a treatment tip (e.g., from an applicator, including a hand-held applicator), may rise extremely rapidly, e.g., exceeding $10^{12}$ V/second or larger when the voltage rise times are in the sub-microsecond or sub-nanosecond range. However, most applicators and pulse generator systems may be able to tolerate only relatively small capacitances (e.g., between 10-20 pF or smaller) and may only employ a single isolation barrier having relatively large capacitance (e.g., greater than 100 pF to 1 nF). The apparatuses and methods described herein may include multi-functional isolation barriers that have a capacitance of about 4-8 pF (e.g., 1.4-2.5 pF, etc.). Such small isolation capacitance is beyond the capability of what is normally required in most pulse generator applications. For example, the apparatuses described herein may include a capacitance of between about 10-20 pF in the overall system; closer to a handpiece the capacitance may be even lower, e.g., between about 3-8 pF. Typically these apparatuses may have a capacitance of less than 20 pF over the various system components and subsystems, as will be described herein. Such low capacitances between the electrical components of an nsPEF apparatus are not typical of existing systems. The multi-functional isolation barriers described herein may also be referred to as high-voltage/low capacitance isolation barriers or as multi-functional high-voltage/low capacitance isolation barriers; for convenience, they may also be referred to herein as "high-voltage isolation barriers" or simply "isolation barriers".

As mentioned, an apparatus, such as an nsPEF apparatus that has multi-functional isolation between various components (e.g., sub-systems) of the apparatus may have a high common mode transient immunity. High common mode transient immunity means that if one side of an interface (e.g., between two or more components/subsystems of the apparatus) changes very rapidly in voltage relatively to another side of the interface, the rapid change will not result in a failure of the system and/or spurious results that may otherwise arise because of the rapid change, which may otherwise result in a high current (including a high current that may otherwise be directed back across the interface, damaging the components of one or both sides of the interface). Although an isolator and/or power supply, or associated components, may isolate standard AC line voltage well, when subjected to fast rise times/slew rates, a typical isolator may fail if the isolation capacitance is too high and thereby allows large currents to flow across the isolation barrier due to the high-frequency content of pulses. The apparatuses described herein may have a much higher common mode transient immunity, so that if one side of the circuitry moves rapidly in voltage relative to the other side, the apparatus may still safely operate without failure, as will be described in greater detail herein.

Any of the components of the pulse generators described herein, including the low-voltage control components, may be well-isolated from the high-voltage, nanosecond signals. This may be implemented in the applicator (e.g., the handpiece or handpiece sub-system), and/or the rest of the system, including the console/pulse generator. In particular, the system may separate any of a system interconnect "zone", a low-voltage component "zone" (e.g., pulse trigger and timing components) and a pulse output zone into separate isolation zones that are separated from each other by multiple cascades of high voltage and extremely low capacitance communications and power supply isolation (e.g., such as isolation capacitances of about 1 pF or less, 5 pF or less, 20 pF or less, 100 pF or less, etc.). In general, these apparatuses may be configured so that the high-voltage, and in some variations high current, nanosecond pulsed output being generated by the pulse generator and delivered by the handheld applicator does not adversely affect the low-voltage components and control signals within the apparatuses.

Any of these apparatuses may alternatively or additionally include an interface board that further isolates any connection between or within the subsystems which may be subject to interference from the high-voltage pulses generated by the pulse generator subsystem. The interface board may include EMI-filtered, transient protected and high-voltage isolation barriers. The interface board may help isolate components within the apparatus (e.g., within the apparatus console, such as all or portions of the pulse generator, treatment controller, the power supply and any user interface CPU, etc.). The interface board may also filter and isolate power and communications to the handpiece subassembly (e.g., the handpiece-to-console connector, the handpiece cable, the handpiece). These techniques may secure the electrical (e.g., galvanic) isolation of component parts even in the presence of very high voltage, nanosecond duration pulses having rise- or fall-times in the picosecond range.

In variations in which the applicator (e.g., including the handle/handpiece) includes low-voltage control circuitry (e.g., for processing one or more inputs, such as a trigger, for identifying/validating a treatment tip, etc.) as well as high voltage and pulsed output, a low-voltage cable (e.g., a low-voltage communications cable) may be connected between the handpiece and the console. One or more low-voltage communications cable(s) may be galvanically isolated from the console and from the handpiece to which it connects, in addition to being isolated from a high-voltage cable that also extends between the console and the handpiece. In some variations the shielded low-voltage cable and the high voltage cable may be twisted together. The low-voltage control cable may be further galvanically isolated by very low-capacitance (e.g., isolation capacitances of about 1 pF or less, 5 pF or less, 20 pF or less, 100 pF or less, etc.) high-voltage DC-DC converters (e.g., isolated power supplies) and digital isolators that can withstand very high transient (e.g., up to or greater than about 7500 V)/differential transients and may also have very low capacitance. Further, even the low-voltage cable (configured to deliver low-voltage, e.g., 15 V or less, 12 V or less, 10 V or less, 7.5 V or less, 5 V or less, etc.) may be configured to 'float' electrically, as described herein.

Described herein are apparatuses (e.g., systems) for delivering nanosecond pulsed electrical energy. Any of these apparatuses (e.g., systems) may include a console that includes one or more of: a system power supply configured to provide system power and pulse generator power; a treatment controller receiving input from one or more user interfaces (e.g., buttons, keyboard, foot pedals, etc.); a nanosecond pulse generator configured to provide at least a 5 kV/μs (e.g., at least about 50 kV/μs, at least about 100 kV/μs, at least about 150 kV/μs, at least about 200 kV/μs, at least about 1000 kV/μs, etc.) of high-voltage pulsed output; an interface board comprising a plurality of electromagnetic interference (EMI)-filtered, transient protected, and high-voltage and very low capacitance isolation barriers, wherein the interface board is in communication with the treatment controller, the system power supply and the nanosecond pulse generator, and wherein all communications and timing signals to or from the nanosecond pulse generator are connected through the EMI-filtered, transient protected, high voltage and low capacitance isolation barriers. The system power supply may be configured to operate from line (e.g., wall) power, and may include power conversion and/or storage circuitry and/or a plug or other connector for connecting to line power. As mentioned, in some variations the power supply may include the high-voltage (pulse generator) power sub-system and the low-voltage (system) power subsystems.

Any of these apparatuses may include a handpiece subsystem. The handpiece subsystem may include: a console-handpiece isolation board, a handpiece cable and a handpiece, wherein the console-handpiece isolation board receives the high voltage pulsed output from the nanosecond pulse generator; system power and/or communications to the handpiece subsystem may be processed separately from the high voltage pulsed power either as part of a different region/portion of the console-handpiece isolation board or separately from the console-handpiece isolation board. For example, the system power and/or communications, which may power the circuitry (e.g., sensors, microcontrollers, inputs, etc.) on the handpiece and/or transmit signals to/from the handpiece, may be further filtered and/or isolated by the interface board (e.g., in the console) through the high-frequency galvanic multi-functional isolation. The handpiece may be configured to connect to the console-handpiece isolation board though the handpiece cable, wherein the handpiece is configured to deliver the high voltage pulsed output.

As used herein, a console may include the treatment controller, the pulse generator (e.g., which may be, but is not limited to, a nanosecond pulse generator), the console-headpiece isolation board, an interface board, as discussed above, and/or the power supply (e.g., power adapters or power conditions). The console may include a housing that may enclose some or all of these components. Alternatively, in some variations the console may not be enclosed, or may include a variety of separate enclosures. For example, some or all of these console components may be separately enclosed or housed from each other.

The treatment controller may include inputs for controlling operation of the system; additionally or alternatively, the applicator, such as a handpiece may include some or all of the inputs. The treatment controller may include one or more processors (e.g., microprocessors), memory, communications circuitry and/or other circuitry for controlling the operation of the apparatus. The treatment controller may adjust the output (the applied pulsed energy) based on one or more fixed or adjustable settings, and/or based on the applicator (e.g., in some variations the sensed applicator tip having a one or more electrodes), and/or based on feedback from pulse measurements within the pulse generator or a pulse measurement subsystem. The treatment controller may communicate with the handpiece.

The treatment controller may be configured as a real-time treatment controller that can respond to safety critical errors or faults in sufficient time (e.g., within about 50 milliseconds or less, within about 20 milliseconds or less, within about 5 milliseconds or less, etc.) to prevent harm to a patient or user. For example, the treatment controller may turn off the apparatus when one or more monitored values is out of a predetermined safety range e.g. if tip-tissue impedance is too high due to insufficient electrode placement).

As mentioned, in any of these apparatuses, the system power supply may be configured to separately provide system power and pulse generator power.

The nanosecond pulse generator may comprise a system interconnect circuit, a low voltage pulse trigger and timing circuit and a pulse output circuit, wherein the system interconnect circuit, the low voltage pulse trigger and timing circuit and the pulse output circuit are separated from each other by one or more high isolation voltage, low isolation capacitance, communications and power supplies, providing multi-functional isolation (e.g., high-frequency and high-voltage isolation) for the pulse output circuit.

The handpiece and handpiece-to-console connector may each comprise a multi-functional isolation power isolation circuitry configured to limit a potential difference across a handpiece circuit board in the handpiece when the handpiece delivers the high voltage pulsed output, which may prevent damage to or interference in the headpiece circuit board electronics.

In any of these variations, the handpiece cable may be electrically floating. For example, the cable may include a floating shield on the low-voltage handpiece power and communications cables to minimize high electric field and in some variations high current inductive coupling to power and/or communications signals.

As mentioned, the handpiece subsystem may further comprise a high-voltage cable (e.g., any high-voltage signal transmission cable(s), including coaxial, twisted pairs, tri-axial, twin-axial, ribbon cables, and/or flexible printed wiring cables) configured to transmit the high voltage pulsed output, wherein the twisted pair of high-voltage cables is configured to minimize high-voltage coupling to the twisted system (e.g., handpiece) power and communications cables, including between a high-voltage, nanosecond pulse cable and a low-voltage control line cable.

Any of these apparatuses may also include a standby switch which may be coupled to the console-handpiece isolation board by an isolated connection, which may control putting the apparatus into a standby mode for later re-activation.

The handpiece may comprise a handpiece circuit board having a microcontroller and RFID reader configured to receive information from a treatment tip on the handpiece.

Any of these apparatuses may also include one or more treatment tips; the treatment tip may include, e.g., one or more needle electrodes. The identity of the treatment tip may be detected by the apparatus, e.g., through the handpiece.

Any of these apparatuses and methods of using them may also include one or more user controls (e.g., foot switch, keyboard, touchscreen, mouse, etc.).

The high voltage (and in some variations high current) pulsed output generated by the nanosecond pulse generator may be configured to have a voltage of greater than about 1 kV, greater than about 7.5 kV, greater than about 10 kV, greater than about 12.5 kV, greater than about 15 kV, etc. The output current may be greater than, for example, 100 A, 150 A, 200 A, 250 A, 300 A, etc.

For example, a system for delivering nanosecond pulsed electrical energy may include: a real-time treatment controller receiving input from one or more user interfaces; a nanosecond pulse generator configured to provide a high voltage pulsed output (e.g., at least about a 5 kV/μs, at least about 50 kV/μs, at least about 100 kV/μs, at least about 150 kV/μs, at least about 200 kV/μs, at least about 1000 kV/μs, etc.), wherein the nanosecond pulse generator comprises a system interconnect circuit, a low voltage pulse trigger and timing circuit and a pulse output circuit, wherein at least one of the system interconnect circuit, the low voltage pulse trigger and timing circuit and the pulse output circuit are separated from each other by one or more multi-functional isolation (e.g., providing a high voltage/low capacitance isolation, a high common model transient immunity, and/or a high dielectric breakdown) communications and power supplies; an interface board comprising a plurality of electromagnetic interference (EMI)-filtered, transient protected and high-voltage isolation barriers, the interface board in communication with the real-time treatment controller, the system power supply and the nanosecond pulse generator, wherein all power to the nanosecond pulse generator and all communications and timing signals to or from the nanosecond pulse generator are connected through the EMI-filtered, transient protected and high-voltage isolation barriers. These sub-systems/components (e.g. the treatment controller, pulse generator, interface board, system power supply/pulse generator power supply, etc.) may be part of a console, as discussed above.

As mentioned above, in some variations the apparatus may include a handpiece subsystem comprising: a console-handpiece isolation board (which may alternatively be part of the console), a handpiece cable and a handpiece, wherein the console-handpiece isolation board receives the high voltage pulsed output (e.g., power) from the nanosecond pulse generator but wherein power and communications to the handpiece subsystem may be filtered and isolated by the interface board. The handpiece may be configured to connect to the console-handpiece isolation board though the handpiece cable; the handpiece and handpiece-to-console connector may each comprise a high-voltage, low capacitance communication and power isolation circuitry configured to limit a potential difference across a handpiece circuit board in the handpiece when the handpiece is delivering the high voltage pulsed output.

Any of these systems may include a system power supply (or power supply adapters or power conditions) configured to separately provide system power and pulse generator power, e.g., separate from the power to the pulse generator that generates the high-voltage, sub-microsecond (including nanosecond) pulses. In some variations, two or more separate power supplies may be provided, e.g., one for the pulse generator and one or more for the rest of the system power.

As mentioned above, the handpiece cable may comprise an electrically floating power (and in some variations communications) cable to minimize high electric field and high current inductive coupling. The handpiece subsystem may include one or more high-voltage cables configured to transmit the high voltage, high current pulsed output, wherein the cable(s) (e.g., a twisted pair of high-voltage cables) is/are configured to minimize high-voltage coupling to the system power and communications cables. The handpiece may include a handpiece circuit board having a microcontroller and RFID reader configured to receive information from a treatment tip on the handpiece and may provide user control and/or feedback via handpiece switches and visual indicators.

Also described herein are methods of using or operating any of these apparatuses. For example, described herein are methods of delivering nanosecond pulsed electrical energy, the method comprising; providing system power and pulse generator power from a system power supply to an interface board comprising a plurality of electromagnetic interference (EMI)-filtered, transient protected, and high-voltage isolation barriers, wherein the interface board is connected to a nanosecond pulse generator; receiving user input from one or more user interfaces through a treatment controller coupled to the interface board; transmitting all communications and timing signals to and from the nanosecond pulse generator through the EMI-filtered, transient protected, and high-voltage isolation barriers of the interface board; isolating and filtering all communications and system power to a handpiece subassembly through the interface board; delivering a high voltage (and/or high slew rate) pulsed output (e.g., at least about a 5 kV/μs, at least about 50 kV/μs, at least about 100 kV/μs, at least about 150 kV/μs, at least about 200 kV/μs, at least about 1000 kV/μs, etc.) from the nanosecond pulse generator to a handpiece of the handpiece subassembly. Any of these methods may also include limiting the potential difference across the handpiece board and ensuring that any voltage or current induced in the cable (which may include a signal-carrying cable and a shield) does not couple into the internal electronics or cables of the rest of the apparatus, where it may otherwise cause damage or disruption of the operation of the apparatus.

For example, described herein are systems for delivering nanosecond pulsed electrical energy. These systems may include: a treatment controller configured to receive input from one or more user interfaces; a nanosecond pulse generator configured to provide at least a high voltage pulsed output; an interface board comprising a plurality of isolation barriers (e.g., high-voltage/low capacitance isolation barriers), wherein the interface board is in communication with the treatment controller, the system power supply and the nanosecond pulse generator, and wherein all communications to or from the nanosecond pulse generator are connected through the isolation barriers. As described above, any of these systems may also include a console-handpiece isolation board and a handpiece subsystem comprising: a handpiece cable and a handpiece, wherein the console-handpiece isolation board receives the high voltage pulsed output from the nanosecond pulse generator and wherein system power and communications to the handpiece subsystem are filtered and isolated by the console-handpiece isolation board, further wherein the handpiece is configured to connect to, and be isolated by the console-handpiece isolation board though the handpiece cable and the handpiece is configured to deliver the high voltage pulsed output.

Also described herein are apparatuses (e.g., systems), and methods of using them, for delivering nanosecond pulsed electrical energy. For example, a system may include: a high-speed digitizer subsystem (e.g., high speed waveform capture unit and processor), a treatment controller receiving input from one or more user interfaces and the high-speed digitizer; a nanosecond pulse generator; an interface board (e.g., including a plurality of electromagnetic interference (EMI)-filtered, transient protected and high-voltage isolation barriers); and a handpiece subsystem comprising: a handpiece cable and a handpiece. The high-speed digitizer is in communication with the interface board and the treatment controller and is configured to sample a pulsed output waveform from the handpiece in real time to monitor and control activity of the system. The treatment controller may be configured to detect a deviation from a predicted applied waveform based on the input from the high-speed digitizer subsystem. The high-speed digitizer subsystem may be coupled to the interface board. The high-speed digitizer may record and process the voltage and current of the high-voltage pulsed output.

The treatment controller may monitor (in real time) the handpiece status, and the pulse generator status, including the high-speed digitizer, and can stop pulse output within a very short time (e.g., 20 milliseconds or less, 10 milliseconds or less, 5 milliseconds or less, etc.) if a handpiece critical status changes, or if the pulse generator status changes, or otherwise if the digitized signal sensed by the high-speed digitizer detects a problem. For example, if an electrode tip becomes detached, if the user released pulse activation button, if the handpiece becomes disconnected from the console, etc. The treatment controller may also stop the pulse output if the pulse generator status shows a critical fault (such as an internal pulse generator power supply parameter being out of a specification-defined value, a safety relay failure, etc.). Within the short time (e.g., 20 milliseconds or less, 20 milliseconds or less, etc.) after a pulse is output by the pulse generator, the pulse waveform may be analyzed by the digitizer and critical pulse metrics may be calculated and communicated to a real-time treatment controller (RTC) 159. The RTC may compare the calculated metrics with the pre-set pulse limits, which may include: treatment, tip type, lesion, and/or body location dependent. If any pulse metric is outside the pre-defined limits, the RTC may pause or stop pulsing within a short time period (e.g., within 20 milliseconds or less, 10 milliseconds or less, etc.) by communicating with the pulse generator well before the next pulse is output, ensuring that any unsafe pulse conditions are restricted to one pulse.

The high-speed digitizer subsystem may include a computer and a high-speed waveform capture unit connected to the rest of the apparatus. The digitizer may sample the voltage and/or current at high sample rate and calculate pulse parameters, communicating these pulse parameters and/or the high-speed sampled pulse voltage and current to the treatment controller to control and monitor treatment pulses. The treatment controller (e.g., a real-time treatment controller) may trigger the digitizer, for example, through a doubly-isolated high-speed digital connection, to capture the pulse voltage and pulse current output waveforms with a high sample rate, sufficient to capture the output voltage and current of the pulse waveform every nanosecond or so (e.g., every 2 nanoseconds, e.g., 50 points of voltage and current for every 100 ns pulse). The digitized waveform may be analyzed by the controller, e.g., using an estimation technique that may use one or more physical models of the cable, applicator tip, and handpiece, such as a fast estimation algorithms and/or one or more pulse metrics to estimate (within a very short time period, e.g., 5 milliseconds or less, 10 milliseconds or less, 20 milliseconds or less, etc.) the applied waveform and/or to detect a problem with the applied waveform. Examples of metrics that may be calculated may include any (or all) of: Average Pulse Output Voltage, Average Pulse Tip Voltage, Peak Pulse Output Voltage (overshoot of the pulse voltage waveform), Peak Pulse Tip Voltage (overshoot of the pulse voltage waveform), Average Pulse Output Current, Average Pulse Tip Current, Peak Pulse Output Current (overshoot of the pulse voltage waveform), Peak Pulse Tip Current (overshoot of the pulse voltage waveform), Pulse Output Voltage Risetime, Pulse Output Voltage Falltime, Pulse Tip Voltage Risetime, Pulse Tip Voltage Falltime, Pulse Output Current Risetime, Pulse Output Current Falltime, Pulse Tip Current Risetime, Pulse Tip Current Falltime, Pulse Output Voltage Pulsewidth, Pulse Tip Voltage Pulsewidth, Pulse Output Current Pulsewidth, Pulse Tip Current Pulsewidth, Cable Impedance, and/or Tip-Tissue Impedance.

In some variations, the controller may calculate one or more pulse sequence metrics, and may determine automatically when to stop a treatment pulse sequence, when the tip-tissue impedance time-course and/or a pulse waveform characteristics time-course indicates that the treatment tip may experience an electrical arc and/or the treatment tip may be improperly inserted and/or the treatment time (e.g., a number of pulses output) may need to be lengthened to achieve good efficacy. A variety of predictive algorithms may be used to aid the nsPEF System in delivering safe & effective treatments, which may be executed in the digitizer and the results communicated to the RTC in real-time (e.g., well-before the next pulse is output from the pulse generator). For example, the digitizer may include predictive algorithms to aid in safety, treatment efficacy (e.g., to minimize pain, etc.), using information from the digitizer. The calculations provided by the controller and/or the digitizer subsystem (e.g., from the samples of the pulse voltage and current at the handpiece) may be used to improve the safety and efficacy of the nsPEF treatment apparatuses described herein. The calculations based on the digitizer output may inform the treatment controller, e.g., whether the electrodes are in sufficient contact with the tissue (tip-tissue impedance) and whether unusual or unsafe conditions exit at the tip-tissue interface or within the high-voltage pulse delivery system. This may include anything from the pulse generator, through the handpiece connector, the handpiece cable, the handpiece, and the treatment tip.

In some variations, a system for delivering nanosecond pulsed electrical energy may include: a real-time treatment controller receiving input from one or more user interfaces and (in some variations) a high-speed digitizer; a nanosecond pulse generator configured to provide a high voltage pulsed output, wherein the nanosecond pulse generator comprises a system interconnect circuit, a low voltage pulse trigger and timing circuit and a pulse output circuit, wherein the system interconnect circuit, the low voltage pulse trigger and timing circuit and the pulse output circuit are separated from each other by one or more multi-function isolation connections; an interface board comprising a plurality of electromagnetic interference (EMI)-filtered, transient protected and high-voltage isolation barriers, the interface board in communication with the real-time treatment controller, the system power supply, the nanosecond pulse generator, and a console-handpiece isolation board, wherein all power to the nanosecond pulse generator and all communications to or from the nanosecond pulse generator are connected through the EMI-filtered, transient protected and high-voltage isolation barriers. Any of these apparatuses may also include a handpiece subsystem comprising: a handpiece cable and a handpiece, wherein the console-handpiece isolation board receives the output from the nanosecond pulse generator but wherein system power and communications to the handpiece subsystem is filtered by the console-handpiece isolation board, further wherein the handpiece is configured to connect to the console-handpiece isolation board though the handpiece cable, further wherein the handpiece and handpiece-to-console connector each comprise a multi-functional communication and power isolation circuitry configured to limit a potential difference across a handpiece circuit board in the handpiece and isolate the handpiece power and communications from the other console subsystems when the pulse generator delivers the high voltage pulsed output to the handpiece.

The isolation barriers may be electromagnetic interference (EMI)-filtered transient protected high voltage isolation barriers. In any of these apparatuses (e.g., systems, devices, etc.) there may be multiple stages of high-voltage/low-capacitance isolation barriers, and the use of these stages may result in a very low isolation capacitance, in which each isolation barrier by itself may be a low-capacitance isolation barrier. The series cascade of multiple low-capacitance isolation barriers results in an extremely low isolation capacitance realized by the system in isolating the pulse output from all other subsystems.

Any of these systems may include one or more system power supply configured to provide system power and pulse generator power. At least one power supply may be configured to separately provide system power and pulse generator power.

The nanosecond pulse generator may include a system interconnect circuit, a low voltage pulse trigger and timing circuit and a pulse output circuit, wherein at least some of the system interconnect circuit, the low voltage pulse trigger and timing circuit and the pulse output circuit are separated from each other by one or more multi-functional isolation communications and power supplies.

The handpiece and the handpiece-to-console connector each comprise a multi-functional isolation communication and power isolation circuitry (e.g., a multi-functional isolation connection) configured to limit a potential difference across a handpiece circuit board in the handpiece and isolate the handpiece power and communications from the other console subsystems when the pulse generator delivers the high voltage pulsed output to the handpiece.

In any of the systems described herein, the handpiece cable may be configured to electrically float (e.g., the cable may be high-frequency galvanically isolated from the console and the handpiece). For example, the handpiece cable may comprise a shield, wherein both the shield and the conductive wires of the cable electrically float. The handpiece may comprise a handpiece circuit board having a microcontroller and RFID reader configured to receive information from a treatment tip on the handpiece. In some variations, the handpiece comprises a microcontroller, an RFID reader, and an encrypted authentication integrated circuit, further wherein the encrypted authentication integrated circuit is configured to ensure authenticity of the handpiece.

Any of these systems may include a high-speed digitizer in communication with the interface board and the treatment controller. The high-speed digitizer may be configured to sample a pulsed output waveform from the pulse generator (and/or the handpiece) in real time to monitor (and/or provide measurements) to control activity of the system.

Any of these systems may include one or more user controls coupled to the interface board. User controls may include controls on the handpiece.

In some variations, the high voltage pulsed output generated by the nanosecond pulse generator may be configured to have a voltage of greater than 15 kV and an output current of greater than 300 A. The nanosecond pulse generator may be configured to provide at least a 10 kV/μs, high voltage pulsed output.

Also described herein are methods for delivering pulsed energy. For example, described herein are methods of delivering nanosecond pulsed electrical energy, the method comprising; providing system power and pulse generator power from a system power supply to an interface board comprising a plurality of high-voltage isolation barriers, wherein the interface board is connected to a nanosecond pulse generator; receiving user input from one or more user interfaces through a treatment controller coupled to the interface board; transmitting all communications to and from the nanosecond pulse generator through the high-voltage isolation barriers of the interface board; isolating and filtering all communications and system power to a console-handpiece isolation board (and/or handpiece subassembly) through the interface board; delivering a high voltage, pulsed output from the nanosecond pulse generator to a handpiece of the handpiece subassembly while providing multi-functional isolation to communication and power transmission at the handpiece and at a console-handpiece isolation board to limit a potential difference across a handpiece circuit board in the handpiece. The high-voltage isolation barriers may each comprise an electromagnetic interference (EMI)-filtered, transient protected, and high-voltage isolation barrier.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
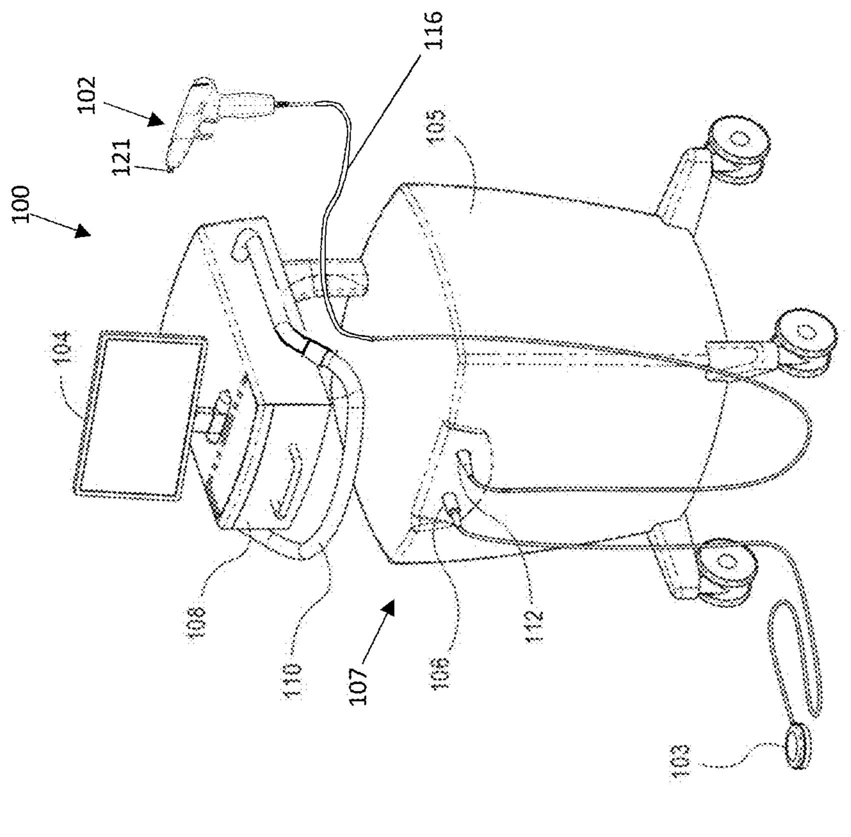
FIG. 1A is an example of one variation of an apparatus (e.g., system) according to the present disclosure.

Described herein are apparatuses (e.g., systems and devices) and methods of delivering nanosecond pulsed electrical fields (nsPEF). In particular these apparatuses and methods may provide enhanced safety and robust operation over even very short (picosecond, nanosecond, etc.) and high voltages (e.g., up to at least 5 kV, greater than 7.5 kV, greater than 10 kV, greater than 12.5 kV, greater than 15 kV, etc.) pulsing. In some variations, these benefits may be accomplished, for example, by electrically isolating much of the apparatus, even including the low-voltage, control and command portions of the apparatus with multi-functional isolation (e.g., multi-functional isolation connections), which may provide high common mode transient immunity (e.g., at least about 5 kV/μs, at least about 50 kV/μs, at least about 100 kV/μs, at least about 150 kV/μs, at least about 200 kV/μs, at least about 1000 kV/μs, etc.), high dielectric breakdown (e.g., greater than about 5 kV, greater than about 5.7 kV, greater than about 6 kV, greater than about 7 kV, greater than about 8 kV, greater than about 9 kV, greater than about 10 kV, between 8-10 kV, etc.), and/or extremely low isolation capacitance (e.g., isolation capacitance of about 50 pF or less, about 40 pF or less, about 30 pF or less, about 20 pF or less, about 10 pF or less, about 8 pF or less, between about 10-20 pF, between about 3-8 pF, etc.).

In many pulsed power applications, there is need for the output of the pulse generator to be well-isolated from control and power supply inputs. Medical devices that apply electrical energy (including in particular those that apply high-power pulses) to the human body for treatment of diseases are required to be highly-isolated to comply with international medical device standards. Described herein are self-contained nanosecond pulse generators that may provide very high isolation of the pulse output terminals from any control or supply inputs. These apparatuses may be configured to provide pulse widths from 1 ns to 1 μs, having rise- and fall-times of about 50 ns or less (e.g., about 20 ns or less, about 15 ns or less, about 10 ns or less, about 5 ns or less, etc.), pulse voltages as high as about 5 kV or more (e.g., about 10 kV or more, about 12 kV or more, about 13 kV or more, about 14 kV or more about 15 kV or more, about 16 kV or more, about 17 kV or more, about 18 kV or more, etc.), very high pulse rise- and/or fall-times or slew rates (e.g., at least about a 5 kV/μs, at least about 50 kV/μs, at least about 100 kV/μs, at least about 150 kV/μs, at least about 200 kV/μs, at least about 1000 kV/μs, etc.), and simultaneously delivering pulse currents of up to about 500 A (or greater). Electrical isolation between components of these systems using traditional techniques may be particularly challenging for such rapid pulses, without distorting the rise and/or fall times (or shape) of the pulses.

In general, any of these apparatuses may be configured to meet or exceed safety standards. For example, the pulse output terminal isolation may pass IEC60601-1 Type BF Applied Part leakage and can pass Type CF Applied Part leakage for cardiac applications.

Any of the nanosecond pulsed electrical fields (nsPEF) apparatuses described herein may include a pulse generator that is configured as a modification of a Marx high-voltage pulse generator. This circuit/system architecture may isolate the pulse output terminals from control and AC power supply inputs and may ensure that pulse timing and triggering circuits which drive the primary side of the pulse transformers are isolated from the system power supply and control inputs.

In a typical pulse generator (including a typical Marx high-voltage pulse generator), the low-voltage pulse timing and triggering circuits may share common circuitry with system low voltage DC supply and system input control signals. When operating this pulse generator at high pulse voltage slew-rates, such as 5 kV/μs to 1000 kV/μs (e.g., 5 kV/μs to 200 kV/11s), even a very small primary to secondary coupling capacitance (isolation capacitance) for the pulse transformers, e.g., approximately 10 pF, can result in high interference currents induced in the pulse timing circuits, as $i=C\,\partial V/\partial t=10\times10^{-12}\cdot 2\times10\ 11=2A$. Such an induced current not only can interfere with pulse timing circuits, but may destroy most low-voltage electronics, such as microcontrollers or MOSFET driver ICs. Described herein are apparatuses (e.g., systems), including in particular high-voltage pulse generators that may avoid these issues.

FIG. 1A illustrates one example of an apparatus (e.g., a system) 100 for delivering high-voltage, nanosecond (or sub-nanosecond) pulses of electrical energy that includes a handpiece 102 and a console (including a pulse generator 107). The system may include one or more user controls/inputs, such as a footswitch 103, and user interface 104. Footswitch 103 may be connected to a footswitch connector mounted in the housing 105, which may enclose the electronic components, through connector 106. The handpiece 102 may include the electrodes (e.g., a removable or swappable electrode tip 121) and may connect to housing 105 and the electronic components therein through a high voltage connector 112. The high-voltage system 100 may also include a storage drawer 108 and a handle 110. The system 100 may also include a holder (e.g., holster, carrier, etc., not shown) which may be configured to hold the handpiece.

A human operator may adjust one or more of: the number of pulses, amplitude, pulse duration, and frequency information, for example, by entering them into a numeric keypad or a touch screen of interface 104; alternatively or additionally, the user may select from one or more predefined protocols that include predetermined parameters. In some embodiments, the pulse width can be varied. For example, a predefined protocol may vary the pulse width, the pulse voltage, the pulse rate, and/or the number of pulses in a treatment.

A microcontroller within the pulse generator (e.g., which may be part of a pulse generator subsystem) may communicate with a real-time treatment controller that sends signals to pulse control elements within system 100. They apparatus may include a handpiece assembly or handpiece subsystem 151, including a handpiece cable 116 and a handpiece (or applicator) 102. The system may also include one or more electrode tips 121 that may be coupled (including removably coupled) to the applicator/handpiece. In some variations, the handpiece cable may include separate low-voltage cables and high-voltage cables that may be wrapped together. The low-voltage cable may pass control signals and/or information to or from the handpiece, while the high-voltage cable may transmit the high-voltage pulsed energy to the tip for delivery to the patient. The apparatuses and methods described herein may provide electrical and/or physical (e.g., multi-functional) isolation between the high-voltage and the low-voltage components, and between internal components, which may be in close proximity and without such isolation may result in potentially damaging induced currents on the low-voltage components.

Figure 1B:
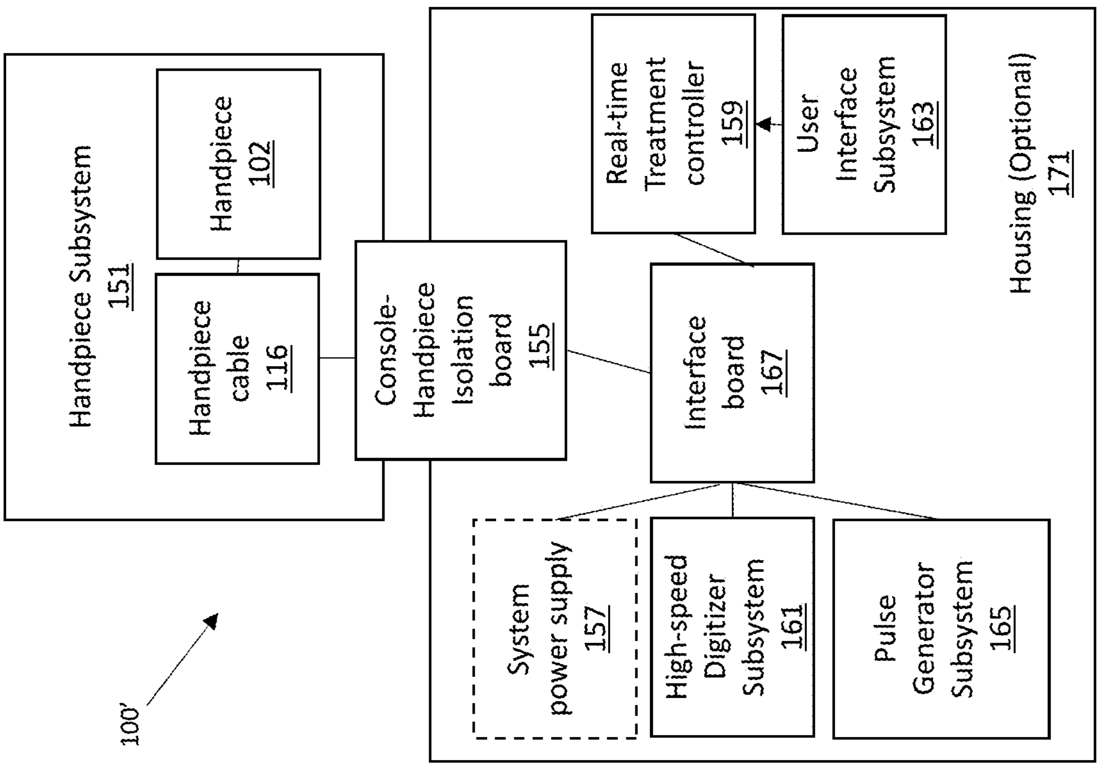
FIG. 1B is a schematic representation of general components of the system, such as the one shown in FIG. 1A.

FIG. 1B is a schematic illustration of various general components of a system for delivering nanosecond pulsed electrical fields (nsPEF), including the one shown in FIG. 1A. In FIG. 1B, the system 100' may be configured for delivering nanosecond pulsed electrical energy and may include a real-time treatment controller 159 that may receive input from one or more user interfaces (e.g., user interface subsystem 163) and a high-speed digitizer subsystem 161 that may sample pulse waveform output to the handpiece. The system of FIG. 1B further includes a pulse generator subsystem 165 (e.g., a nanosecond pulse generator subsystem) configured to provide the high voltage (e.g., at least 5 kV/μs, at least 10 kV/μs, at least 2 kV/μs, at least 50 kV/μs, at least 100 kV/μs, at least 150 kV/μs, at least a 200 kV/μs, at least a 1000 kV/μs, etc.), and in some cases high current, pulsed output. The nanosecond pulse generator may include a system interconnect circuit section, a low voltage pulse trigger and timing circuit section, and a pulse output circuit section (not shown), wherein the system interconnect circuitry, the low voltage pulse trigger and timing circuity and the pulse output circuitry may be separated from each other by multi-functional isolation as is will be described in greater detail below in reference to FIG. 2. The pulse generator may be a modified Marx high-voltage pulse generator. Housing (optional) 171 may enclose some or all of these components.

In any of these systems, system operation and conditions may be monitored by subsystems within the interface board and/or the pulse generator subsystem.

The interface board 167 may include a plurality of electromagnetic interference (EMI)-filtered, transient protected and high-voltage isolation barriers. The treatment controller (e.g., a real-time treatment controller 159), a system power supply 157 and a nanosecond pulse generator subsystem 165 may all connect to and/or through the interface board, as shown in FIG. 1B. In some variations power to the pulse generator subsystem and/or triggering for the high-speed digitizer subsystem 161 is connected and isolated through the EMI-filtered, transient protected and high-voltage isolation barriers, which may be part of the interface board 167. Any of the systems described above may include a handpiece subsystem 151 that in turn may include a console-handpiece isolation board 155, a handpiece cable 116 and a handpiece 102, wherein the console-handpiece isolation board may receive the high voltage (and optionally high current) pulsed output from the pulse generator subsystem 165, but further wherein the system power and communications to the handpiece subsystem may be filtered and isolated by the interface board. The handpiece 102 may be configured to connect to the console-handpiece isolation board though the handpiece cable, further, the handpiece and handpiece-to-console connector may each comprise a high-voltage, low capacitance communication and power isolation circuitry (which may be referred to as a multi-functional isolation connection) configured to limit a potential difference across a handpiece circuit board in the handpiece when the handpiece is delivering the high voltage pulsed output, as will be described below.

In some variations, the handpiece cable 116 may be doubly isolated. For example, the power and communications cable (e.g., a portion of the handpiece cable) may be isolated from the console, and the power and communications cable may be isolated from the handpiece 102 (e.g., the handpiece circuitry). Thus, the handpiece cable may be electrically floating. Because there is a finite speed for cables carrying electrical signals (e.g., approximately 70% the speed of light), the ends of a long cable may have different potential differences. This may result in a high current flow where a high voltage pulse is applied to the cable. The handpiece cables 116 described herein may isolate the hand piece from cable as well as the cable from the console (through the console-handpiece isolation board 155). Thus, any large potential difference that may occur from the treatment tip to the console may appear across the multi-functional isolation barriers and may protect the handpiece 102 (e.g., the electronics board in the handpiece) from any large voltage differences that may otherwise develop across the handpiece board. This may be achieved by electrically floating the handpiece cable. The system may provide interfaces at both ends of the cable that are configured to include compact filtering. Although the cable is electrically floating, the system may include one or more transient suppressors (e.g., transient suppression circuitry) that may, e.g., if cable approaches a limiting voltage (e.g., 3-4 kV), prevent the voltage from going too high (e.g., greater than 3-4 kV). All of the circuit traces that come between any device and the cable on the isolated side may configured to be as small as possible. Thus, substantially all of the wires and shields of the handpiece cable may be completely floating. All of the wires within the cable as well as the shielding may be electrically floating. Alternatively, in some variations, the hand piece may translate information and communications via optical fiber.

In FIG. 1B, the system also includes a system power supply 157 that is configured to provide both system power and pulse generator power; in some variations, multiple power supplies may be used to separately provide power to the pulse generator and other portions of the system. In some variations a single power supply that includes internal isolation may provide power to both the pulse generator and the other components of the system (e.g., the system power).

For example, a nanosecond pulsed electrical field treatment system, such as those described herein, may be configured to provide pulses having a pulse width of between about 100 ns to 1000 ns, at a pulse rate of between about 0.01 to 10 pulses/sec. The voltage may be between about 5-20 kV (e.g., between 5-18 kV, between 10-18 kV, etc.) such as between 7-15 kV. The peak pulse current may be, e.g., between 50 A-600 A (e.g., between 50-500 A, between 70-300 A, etc.). For example, the pulse current may be about 500 A maximum at about 15 kV (e.g., 7.5 Megawatts peak pulse power), e.g., between 70 A to 300 A over the entire pulse range.

The multi-functional isolation may be achieved between all or some of the pulse generator subsystem by isolating the pulse generator power ($V_{pg}$) from the overall system power ($V_{sys}$) to minimize interference to the other internal subsystems. In some variations, the pulse transformer and pulse transformer driver layout may be configured to minimize coupling capacitance from the high voltage (HV) pulse section (e.g., 18 kV max pulse voltage) to the low voltage (LV, e.g., ~20 V) driver section.

In general, the systems described herein may be designed with separation of functions, so that each subsystem is optimized for its function and configured to ensure that safety-critical functions are not mingled with non-safety-critical functions. For example, the graphical user interface subsystem (GUI) may be configured as the only subsystem that communicates with the outside world and a touch-screen. It may not participate in any real-time treatment control and may only communicate treatment parameters to the real-time controller, which updates the treatment status to the GUI for user display.

The real-time treatment controller subsystem may control and monitor safety and efficacy critical subsystems, such as the pulse generator subsystem 165, the digitizer (high speed digitizer) subsystem 161, and the handpiece subsystem 151. The real-time treatment controller's software may monitor (in real time) the handpiece status and pulse generator status and can stop pulse output within a very short time (e.g., 20 milliseconds or less, 10 milliseconds or less, 5 milliseconds or less, etc.) if a handpiece critical status changes; for example, if an electrode tip becomes detached, if the user released pulse activation button, if the handpiece becomes disconnected from the console, etc. The treatment controller may stop the pulse output if the pulse generator status shows a critical fault (such as an internal pulse generator power supply parameter being out of a specification-defined value, a safety relay failure, etc.). Within the short time (e.g., 20 milliseconds or less, 20 milliseconds or less, etc.) after a pulse is output by the pulse generator, the pulse waveform may be analyzed by the digitizer and critical pulse metrics may be calculated and communicated to a real-time treatment controller (RTC) 159. The RTC may compare the calculated metrics with the pre-set pulse limits, which may include: treatment, tip type, lesion, and/or body location dependent. If any pulse metric is outside the pre-defined limits, the RTC may pause or stop pulsing within a short time period (e.g., within 20 milliseconds or less, 10 milliseconds or less, etc.) by communicating with the pulse generator well before the next pulse is output, ensuring that any unsafe pulse conditions are restricted to one pulse.

A high-speed digitizer subsystem 161 may include a computer and a high-speed waveform capture unit connected to the rest of the apparatus. The digitizer may sample the voltage and current at high sample rate and calculate important pulse parameters, communicating these pulse parameters and the high-speed sampled pulse voltage and current to the Real-Time Treatment Controller 159 to control and monitor treatment pulses. The digitizer may be triggered, for example, through a doubly-isolated high-speed digital connection, when the pulse generator is active, to capture the pulse voltage and pulse current output waveforms with a high sample rate, sufficient to capture the output voltage and current of the pulse waveform every nanosecond or so (e.g., every 2 nanoseconds, e.g., 50 points of voltage and current for every 100 ns pulse). The controller (e.g., real time treatment control) may control the pulse generator.

This pulse waveform may be quickly analyzed using, e.g., one or more physical models of the cable, applicator tip, and handpiece, using a variety of fast estimation algorithms and pulse metrics to quickly calculate (within a very short time period, e.g., 5 milliseconds or less, 10 milliseconds or less, 20 milliseconds or less, etc.) the applied waveform. Examples of metrics that may be calculated may include any (or all) of: Average Pulse Output Voltage, Average Pulse Tip Voltage, Peak Pulse Output Voltage (overshoot of the pulse voltage waveform), Peak Pulse Tip Voltage (overshoot of the pulse voltage waveform), Average Pulse Output Current, Average Pulse Tip Current, Peak Pulse Output Current (overshoot of the pulse voltage waveform), Peak Pulse Tip Current (overshoot of the pulse voltage waveform), Pulse Output Voltage Risetime, Pulse Output Voltage Falltime, Pulse Tip Voltage Risetime, Pulse Tip Voltage Falltime, Pulse Output Current Risetime, Pulse Output Current Falltime, Pulse Tip Current Risetime, Pulse Tip Current Falltime, Pulse Output Voltage Pulsewidth, Pulse Tip Voltage Pulsewidth, Pulse Output Current Pulsewidth, Pulse Tip Current Pulsewidth, Cable Impedance, and/or Tip-Tissue Impedance.

Pulse sequence metrics may be calculated, and may provide the apparatus with the ability to determine automatically when to stop a treatment pulse sequence, when the tip-tissue impedance time-course and pulse waveform characteristics time-course predict that the treatment tip may experience an electrical arc and/or the treatment tip may be improperly inserted and/or the treatment time (number of pulses output) may need to be lengthened to achieve good efficacy. A variety of predictive algorithms may be used to aid the nsPEF System in delivering safe & effective treatments, which may be executed in the digitizer and the results communicated to the RTC in real-time (e.g., well-before the next pulse is output from the pulse generator). For example, the digitizer may include predictive algorithms to aid in safety, treatment efficacy (e.g., to minimize pain, etc.), using information from the digitizer. The calculations provided by the Digitizer (e.g., from the samples of the pulse voltage and current at the handpiece) may be used to improve the safety and efficacy of the nsPEF treatment apparatuses described herein. The calculations from the digitizer information may inform the real-time treatment controller, e.g., whether the electrodes are in sufficient contact with the tissue (tip-tissue impedance) and whether unusual or unsafe conditions exit at the tip-tissue interface or within the high-voltage pulse delivery system. This may include anything from the pulse generator, through the handpiece connector, the handpiece cable, the handpiece, and the treatment tip.

Thus, any of the apparatuses described herein may perform waveform analysis on the waveforms being delivered to the subject. A therapeutic voltage level may be achieved based on the time and intensity of the applied stimulation, which may be monitored using the digitizer, and used to adjust the activity of the apparatus; the deposition of energy may be balanced, so that sufficient energy is applied to be effective to disrupt cell membranes in target tissues, but without heating or otherwise damaging surrounding (e.g., non-target) tissue.

As illustrated in FIG. 1B, internal components (e.g., between different sub-systems and/or within a particular sub-system) of the apparatus may be electrically isolated by multi-functional isolation. For example, a pulse generator subsystem may include three or more circuit regions (e.g., sub-circuits or circuit sections) which may be isolated from each other by multi-functional isolation connections, such as a system interconnect circuit section, a low-voltage circuit section (also referred to herein as a pulse triggering and timing section), and/or a pulse output circuit section. For example, the pulse generator subsystem may include a system interconnect circuit section that contains connections to the interface board. These connections may be designed to withstand severe voltage transients, which can occur even with the extreme isolation of the pulse output circuit. All communications and safety hardware "pulse disable" connections may be made through the system interconnect circuit section. The pulse triggering and timing section may contain a microcontroller which may be in constant communication with the real time controller (RTC, e.g., through the Interface board) and may control all pulse formation, triggering, pulse rate, etc., and may contain the pulse transformer driver circuits that distribute the pulse trigger to the primary side of the multiple (e.g., 21 or more) high-voltage isolated pulse transformers. The pulse triggering and timing section may also have a safety critical feature, e.g., a feature that (if communication is lost or corrupted to the RTC), stops pulsing within a maximum of three or fewer output pulses. The pulse triggering and timing section may also contain a safety critical hardware pulse disable; the pulse disable may be a single wired connection that the RTC can use to as an emergency disable to stop pulsing as a final safety backup. This pulse disable may be connected directly to the pulse triggering circuit, so even if the microcontroller is disabled or malfunctioning, the RTC can stop pulsing within 1 pulse period.

The pulse output circuit section, which may also be referred to herein as a high-voltage circuit section (e.g., HV circuit section), may contain a microcontroller in constant communication and coordination with the real-time controller, the power MOSFETs, secondary side of the pulse transformers, isolated high-voltage power supply (e.g., 6 kV power supply), a safety "charge dump" relay (which may discharge the high voltage (HV) capacitors that make up stages, such as Marx pulse stages), and numerous protection circuits to ensure that the MOSFETs are protected even under 28 kV overvoltage (e.g., from a 15 kV pulse into an open-circuit at the treatment tip), −15 kV/600 A overcurrent (e.g., from an arc or short at the treatment tip), and from coupling of the HV output to the gate-source control pins of the MOSFETs.

The HV circuit section microcontroller may control and monitor the charge voltage (e.g., a voltage to which the capacitors are charged before the stages are switched to create the output pulse) and may monitor the charge current, which may be the current that the isolated HV supply (e.g., in some variations up to 6 kV) outputs to charge the HV capacitors. A higher than normal Charge Current may indicate the health of the HV circuit section components, as a higher than normal charge current may be indicative of failure or can be used as a failure predictor, if monitored by the nsPEF System over many uses.

The HV circuit section may also contain the charge dump relay, which can be configured to safely discharge the HV capacitors very quickly (e.g., within 3 seconds or faster, e.g., within 2 seconds, within 1 second, etc.), but may discharge them in a controlled manner; the high-voltage/high-power discharge resistors may be configured to discharge fast enough to render the HV circuit section safe in the event of a failure, but not so fast that it induces a high-voltage at the treatment tip, which can be a problem if the HV capacitors are discharged too quickly.

As described above, any of these apparatuses may include an interface board. The interface board may contain power management circuits, a microcontroller to monitor and control the power management circuits, power supply filtering, transient and EMI suppression components, and may further isolate for digitizer triggering from the pulse generator subsystem.

Figure 2:
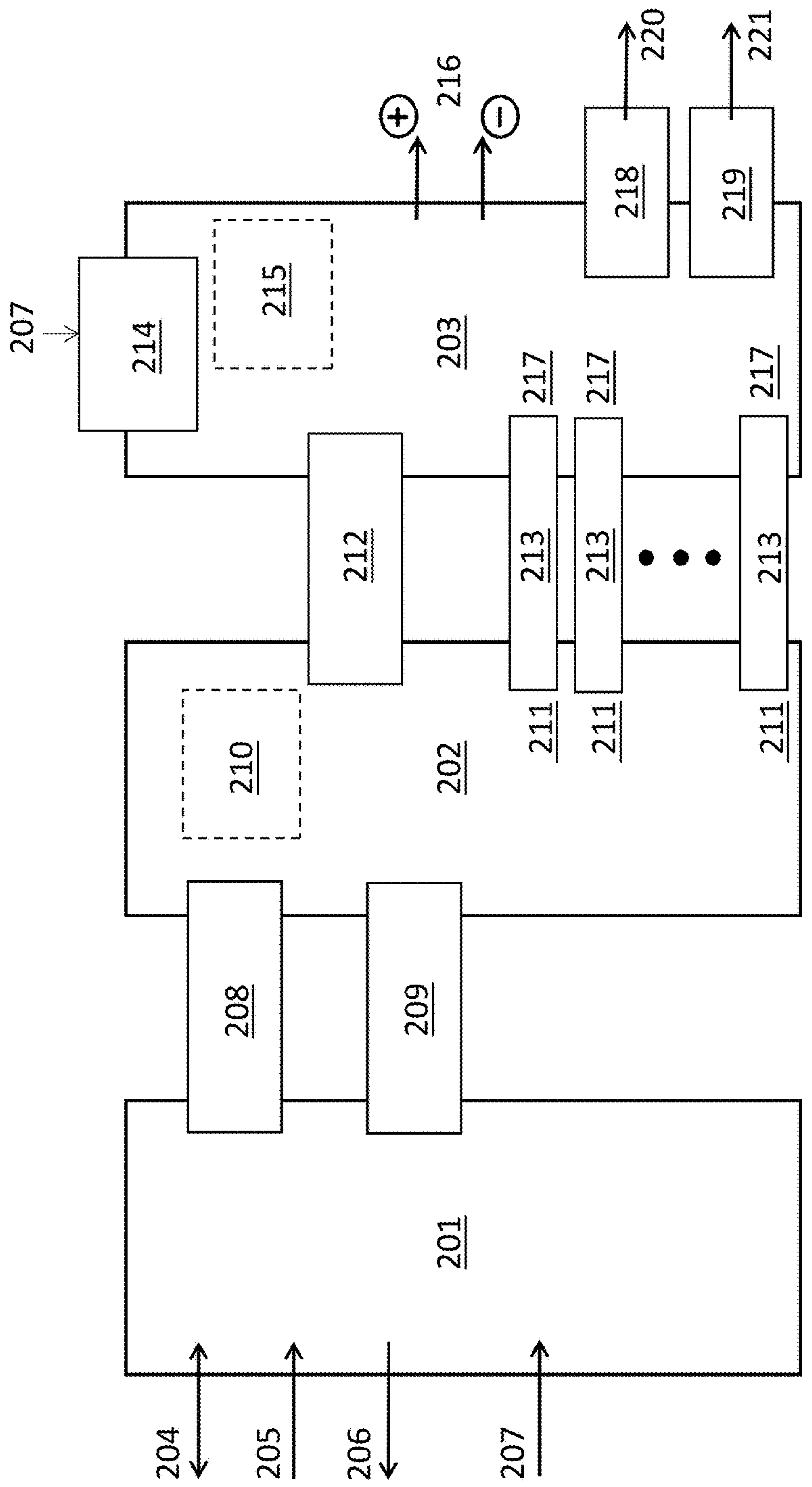
FIG. 2 illustrates a block-diagram form including schematics of a pulse generator subsystem of an exemplary nanopulse generator (e.g., nsPEF generator) having several stages of multi-functional isolation, as described.

FIG. 2 illustrates a block-diagram form including schematics of the three major circuit sections describe above: a systems interconnect circuit section 201, a pulse triggering and timing section 202 (also referred to as "timing/triggering circuit section 202"), and a high voltage/optionally high current pulse generation section 203. The first circuit, e.g., the systems interconnect circuit section 201, may correspond to the input/output of the supervisory control system and the common system power supply, such as serial communications input 204, a pulse enable/disable input 205, a digitizer trigger output 206, and a pulse generator power source 207. The second circuit, e.g., the pulse triggering and timing section 202, may contain circuits (e.g., circuit regions) that drive the pulse transformers and maintain precise timing of the nanosecond pulses (e.g., a triggering/timing control circuit or microcontroller 210). The third circuit, e.g., the high-voltage/optionally high-current pulse circuit section 203 (or high-voltage pulse output circuit section), may contain the high-voltage power supply (or high voltage control or high voltage microcontroller 215), high-voltage/high-current switches or switching elements (e.g., MOSFET HV switch 217) connected to a pulse transformer 213 which is in turn connected to a transformer drive 211 on the second (e.g., timing/triggering circuit section 202), protection circuits, and output voltage and current monitoring devices (e.g., isolated pulse current sensor 218 and isolated pulse voltage sensor 219). The isolated pulse current sensor 218 may output a scaled, isolated pulse current, and the isolated pulse voltage sensor 219 may output a scaled isolated pules voltage. The high-voltage circuit section 203 may include the high voltage output terminals 216 and may receive power from the pulse generator power source 207 via an isolated high-voltage power module 214.

In FIG. 2, the system interconnect circuit section 201 contains the control and communications connections. For additional isolation, filtering, and voltage level translation, these wires and cables connect to the interface board before being further connected to the real-time treatment controller. The system interconnect circuit section may also contain a digitizer trigger output 206, which synchronizes the digitizer pulse voltage and current waveform sampling with the high-voltage pulse-output timing. During operation the system interconnect circuit section 201 may receive commands from the real-time controller and sends status messages in return using the serial communications input 204. The pulse generator may be controlled through this connection, which receives commands to set, e.g., pulse width, pulse rate, pulse voltage, and/or number of pulses in a pulse sequence. For safety, if the timing and triggering control circuit fails, a hardware pulse enable/disable input 205 is configured to bypass the timing and triggering control circuit and can disable pulsing. This pulse enable/disable signal may originate at the real-time controller. The system interconnect circuit section 201 and the pulse triggering and timing section 202 may obtain power from the pulse generator power source 207 with power isolation between these circuit sections provided by a power isolator 209. All digital input and output 204, 205, 206 may be conveyed to the pulse triggering and timing section 202 through a high-voltage, low-capacitance, digital isolator 208 (e.g., a multi-functional isolation circuitry or connection).

Thus, the pulse triggering and timing section 202 may be isolated from the system interconnect circuit section 201 by a high-voltage, low-capacitance digital isolator 208 and may receive power from a high-voltage, low-capacitance power isolator 209. The pulse triggering and timing section 202 may contain triggering/timing control circuits 210, which may include a microcontroller that generates timing and triggering signals that drive the pulse transformers 213 and communicate with the high-voltage pulse output circuit section 203 over a high-voltage, low-capacitance digital isolator 212 (e.g., a multi-functional isolation circuitry or connection). The control circuits may also monitor the isolated power from a high-voltage, low-capacitance power isolator 209 and may communicate measured power supply levels to the real-time controller for safety monitoring. The pulse triggering and timing section 202 may also contain a low leakage inductance pulse transformers that drives the high-voltage switching circuits contained in the high-voltage pulse output circuit section 203.

The pulse transformers 213, which may be configured to provide low-capacitance isolation, and/or may be configured to provide low-capacitance isolation with withstand voltages, e.g., from about 1 kV to over 100 kV or more. The pulse transformers 213 may be replaced in alternative implementations with high-voltage isolation low-capacitance driver circuits such as opto-electronics, series-connected high-voltage digital isolators (where each isolator may provide, e.g., 1 kV to 5 kV, but the series combination may provide 22 kV or more high-voltage withstand isolation).

The pulse transformers 213 may deliver the triggering signal from the timing/triggering circuit section 202 to the high voltage output terminals 216 with minimum skew (difference in output timing) and minimum jitter (difference in output timing from one trigger signal output to another).

The high-voltage pulse output circuit section 203 may be isolated from the pulse triggering and timing section 202, from the system interconnect circuit section 201, and from the pulse generator power source 207. The high-voltage pulse output circuit section 203 may contain fast high-voltage and high-current capability switching elements 217 connected to pulse transformers 213 that are designed to withstand the charging voltage, which can range, e.g., from 50 V to 10 kV or more, and may be the output of the isolated high voltage power module 214. In some variations, the switching elements 217 are MOSFETs, but may be any fast switching component that can withstand high-voltage and switch high-current, including parallel and series combinations of such switching elements to increase the high-voltage withstand and increase current handling. Alternative implementations of these switching elements 217 may include, but are not limited to, insulated gate bipolar transistors (IGBTs), spark gaps, Thyristors, Bipolar Junction Transistors (BJTs), etc. The term "fast switching" may describe any switching component that has turn-on and turn-off times of, e.g., about 50 ns or less, about 20 ns or less, about 10 ns or less, etc.

The high-voltage pulse output circuit section 203 may include a microcontroller 215 managing the stage charging voltage by adjusting the voltage from the isolated high-voltage power module 214. The microcontroller 215 (e.g., the microcontroller for managing the high-voltage module) may communicate with the pulse triggering and timing section 202 through a high-speed high-voltage low-capacitance digital isolator or communications interface 212. The microcontroller 215 may receive commands from the microcontrollers 210 to adjust the pulse voltage output at terminals 216 and safety relays and components that ensure the high-voltage is removed or reduced to safe levels when not pulsing.

The high-voltage pulse output circuit section 203 may also include an isolated pulse current sensor 218 and pulse voltage sensor 219. The isolated pulse voltage sensor 219 may output (at coaxial connector 220) a scaled version of the pulse output voltage appearing at pulse output terminals 216. This voltage waveform may then input to the digitizer subsystem to record a pulse voltage output waveform Similarly, the pulse current sensor 218 may output (e.g., at coaxial connector 221) a voltage corresponding to the pulse output current waveform at pulse high voltage output terminals 216 and this waveform may also input to the digitizer to record the pulse output current.

Thus, as shown and described in FIG. 2 and similar systems, each circuitry sub-region (e.g., the system interconnect circuit section, isolated timing/triggering circuit section, and the isolated high-voltage pulse output) may be connected by a multi-functional isolation circuitry. For example, the system interconnect circuit section 201 and the isolated timing/triggering circuit section 202 may be connected by the digital isolator 208 and the power isolator 209. In turn the isolated timing/triggering circuit section 202 may be connected by the digital isolator 212 and each of the pulse transformers 213, connected between a transformer driver 211 and an HV switch (e.g., MOSFET) 217.

In the apparatuses described herein, including using the schematic shown in FIG. 2, high isolation (e.g., 60601-1 Type CF Applied Part isolation) is obtainable and may be achieved by having an optional extra stage of isolation between the third circuit (e.g., the high-voltage pulse generation circuit), and the system DC supply and system control inputs.

In some variations, the isolation between the first and second circuits may consist of a high-voltage isolated DC power supply module and high-voltage isolated communication ICs having a total parallel capacitance of, for example, about 24.4 pF (e.g., between about 20 pF and 30 pF, between about 15 pF and 32 pF, between about 22-27 pF, etc.). This extra isolation may reduce the capacitance from the High-Voltage circuit, which may have a direct connection to the patient.

Additional isolation may be provided by the isolated third circuit DC-DC power supply, from the patient-connected high-voltage pulse generation section to the system or AC power supply inputs. This DC-DC Power Supply may create both the low-voltage to power the low-voltage power supply control and monitoring circuits and the internal low-voltage to high-voltage DC-DC power supply.

Thus, FIG. 2 illustrates an example of a pulse generator subsystem having multi-functional (and multi-stage) isolation. In this example, each circuit section may also contain protection devices and a discharge resistor to avoid a high voltage differential between components due to charge build up during operation.

As will be described in greater detail below, in reference to FIG. 3, in some variations of the pulse generators described herein, there may be multiple interconnected pulse transformers. The individual pulse transformers may have a low primary to secondary (e.g., isolation) capacitance (e.g., capacitances may be 10 pF or less, 20 pF or less, 40 pF or less, etc.), the presence of multiple pulse transformers in parallel may have the effect of multiplying this capacitance. For instance, if the primary to secondary capacitance of an individual pulse transformer is 10 pF, then the total capacitive coupling due to the pulse transformers may be the number of pulse transformers times 10 pF=x pF, which may be a significant percentage of the capacitive coupling required to meet some regulatory standards for medical equipment (e.g., 60601-1 Type BF leakage standards, the leakage must be less than about 92.4 pF to meet Type CF leakage standards). This capacitance may be mitigated by the additional isolation between the triggering/timing control circuits 210 and the system interconnect circuit section 201 that may connect to the interface board.

A nanosecond pulsed electric field (nsPEF) medical device may present unique design challenges compared to other medical devices which directly use electric fields on the human body. For example, their high peak power (e.g., megawatts), short pulse widths (e.g., nanoseconds), and fast turn-on and turn-off times (e.g., nanoseconds), along with the requirement that they adhere to IEC 60601 medical device safety standards, such as applied part leakage current limits, may incorporate innovations in system and circuit design including any of those described herein.

The apparatuses described herein may operate significantly differently than other medical devices that may generate PEF (including nsPEF). For example, RF electrosurgical devices or electroporation devices typically operate an output power of less than 500 W and typically no more than a few hundred volts. RF electrosurgical devices can be pulsed, but their pulses typically have slow turn-on and turn-off times time (e.g., typically 100 μs to several ms). As a result, they can be more easily shielded from other electronics in the electrosurgical device, and in some variations, inexpensive, easily available, capacitors can be used to couple the RF power to the patient. Similarly, electroporation devices can have higher voltages than RF electrosurgical devices, but typically output less than 5 kV and have much longer pulse widths than nsPEF devices (100 μs to 10 ms), with turn-on and turn-off times (10 μs to 1 ms), and peak power of less than 250 KW.

In contrast, the nsPEF medical devices described herein may, in certain implementations, operate with peak output power of 7.5 MW with output voltages greater than 15 kV, output currents greater than 300 A, and voltage turn-on and turn-off rates greater than 200 kV/μs (e.g., greater than 1000 kV/μs), although they must still must meet IEC 60601 standards for Type BF (body floating) or Type CF (cardiac floating) isolation from the Applied Part (the treatment connection to the body). Traditional RF electrosurgical and electroporation medical device architectures cannot be used with these power levels due to the need for substantial output coupling capacitance with very high voltage ratings.

Additionally, in the absence of the novel configurations, techniques and methodologies of the present disclosure, the fast turn-on and turn-off times and high-voltage present during the nsPEF pulse may otherwise cause EMI problems within the nsPEF device, such that a treatment pulse might destroy the nsPEF system electronics due to induced currents or voltages.

In general, the nsPEF system architecture of the present disclosure may resolve the difficulties of both high output isolation required for the medical device (IEC 60601 Type BF or Type CF) and the acceptable EMI necessary for the device to function in the presence of nsPEF pulses. FIG. 3 schematically illustrates one example of an architecture of a nanosecond pulsed electric field (nsPEF) system. In this example, the isolated pulse generator 307 may include the at least three isolation zones (circuitry regions) within the pulse generator as described above in FIG. 2 (e.g., system interconnect, low voltage pulse trigger and timing, and pulse output). These may be separated from each other by multi-functional isolation (e.g., high isolation voltage low capacitance isolation), communications and power supplies, ensuring that, for example, the high-voltage output from the isolated pulse output circuit to the handpiece connector has no, or minimum (e.g., within acceptable limits), effect on the low-voltage pulse generator electronics or the other subsystems within the nsPEF device.

Figure 3:
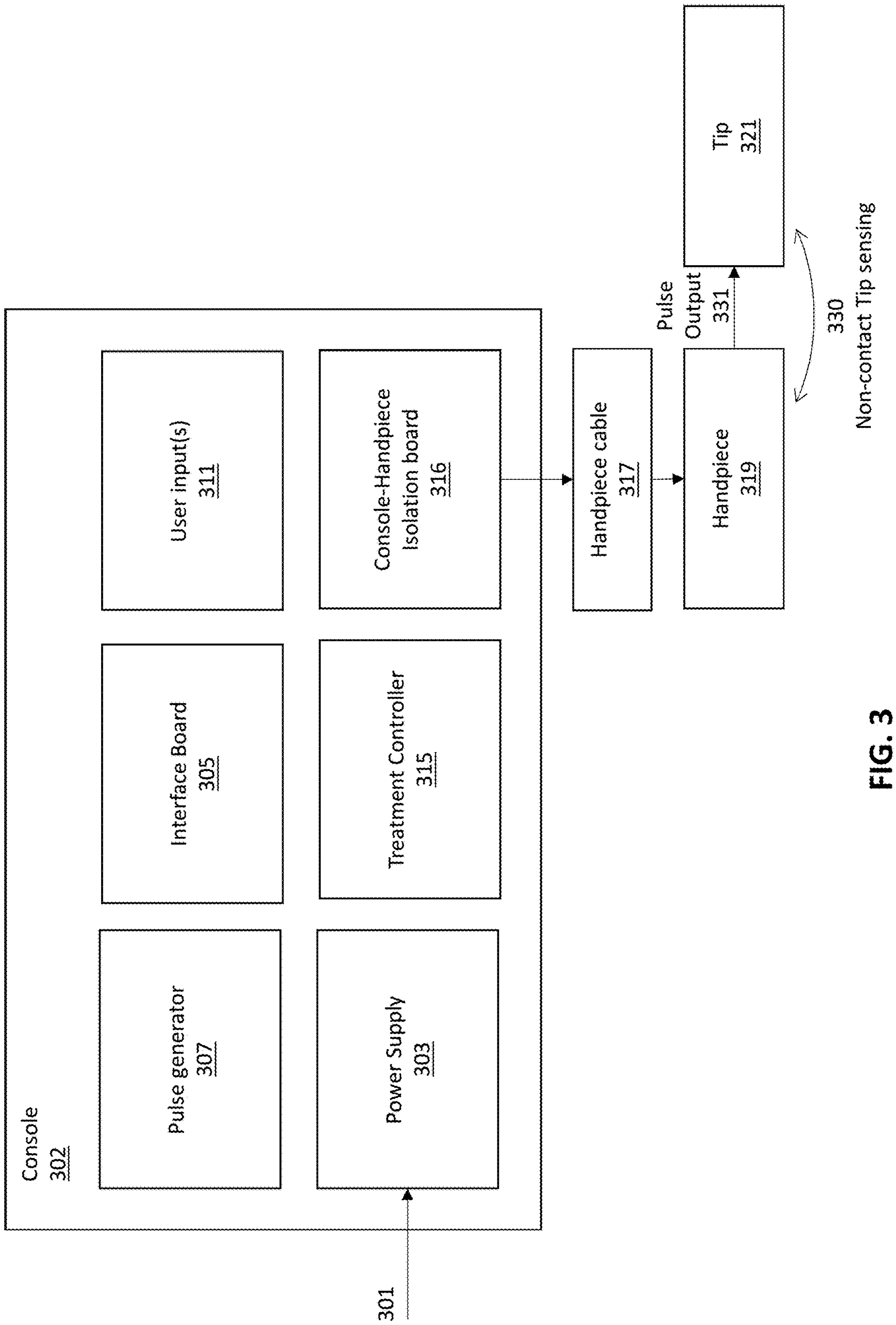
FIG. 3 illustrates one example of an architecture of an nsPEF apparatus having multi-functional isolation as described herein.

As shown in the example of FIG. 3, the system may include one or more power supplies 303 that provides isolated power to either the overall system and/or to the pulse generator; the power may be applied through an interface board 305. As mentioned above, the interface board 305 may provide EMI and transient protection and multi-zone power and signal isolation. In any of the apparatuses descried herein, the interface board 305 may further and more rigorously isolate the component portions of the apparatus. The interface board may further isolate any connections with the pulse generator 307 and ensure that any communication signals that interact with the pulse generator are connected only through EMI-filtered, transient protected, and high-voltage isolated barriers. The interface board 305 may filter and isolate power and communications to the handpiece subsystem 317, 319, and 321, which may connect to the rest of the system through a console-handpiece isolation board 316. The handpiece subsystem may include the handpiece cable 317 (which may also be coupled to or integral with a handpiece-to-console connector), handpiece 319 and tip (also referred to as "treatment tip") 321. The handpiece cable 317 may carry the same pulse generator output 331 (e.g., a 5 to 200 kV/μs, high-voltage output) and may be subject to the destructive EMI that can result. Thus, the system may also include high-voltage, low-capacitance communications and power isolation at the console-handpiece isolation board 316. Any of these apparatuses may also include a floating-shield on a cable (such as combined twisted power and communications cables) that is continued to the handpiece cable (e.g., through a console-to-handpiece connector). As discussed above, the handpiece cable 316 may be electrically floating, including but not limited to any cable component including the shielding. Any appropriate high-voltage isolation barrier may be used. A high-voltage isolation barrier may include, e.g., transient voltage suppressor (TVS) diodes, a linear transformer (e.g., high-voltage isolated DC/DC converter, isolation transformers, etc.), etc.

The system shown in FIG. 3 may also include a user input 311, such as a user interface control, e.g., buttons, keyboard, and/or touchscreen. It may also include a non-contact tip sensing 330.

As already described above, the apparatus may include a real-time treatment controller 315 that may communicate with a high speed digitizer, e.g., to control the application of pulses by the treatment applicator (e.g., combined handpiece and the tip), while receiving input from the high speed digitizer. Any components that are mounted near the Pulse Generator output cables, such as a standby switch (not shown), may also be isolated as described herein.

In some variation the handpiece cable 317 comprises a high-voltage cable(s) and one or more low-voltage cables which may be configured to minimize high-voltage coupling to the shielded low-voltage communications and power wires and may provide an impedance match to the patient-applied treatment tip.

The design features described herein may ensure that the handpiece 319, including a handpiece circuit board, which may include a microcontroller, RFID reader and other electronics, and may have the high-voltage, optionally high-current pulse output cable in close-proximity, has very little potential difference across the board that is the cause of EMI-induced failures. In the example shown in FIG. 3, and in greater detail in FIGS. 4A-4C, the apparatus may include a two-stage isolation from the internal nsPEF subsystem connections to the handpiece prevent the transmission of induced currents from the handpiece cable and the handpiece back to the sensitive electronics within the system enclosure.

The handpiece and handpiece connection subsystem may also be configured to ensure that the nsPEF applied part (e.g., where the applied part may refer to the part of the device that is connected to the patient to provide treatment or monitoring, such as the handpiece or treatment tip) carrying the nanosecond high-voltage treatment pulse, is well-isolated from the low-voltage communications and power cables. The capacitive coupling of the high-voltage cables that are directly connected to the treatment tip, to the low-voltage cables within the handpiece cable can be up to 200 pF, which exceeds the Type CF standard and reduces the margin for compliance with Type BF standards. The low-capacitance communications and power interface within the console-handpiece isolation board ensures that the capacitive coupling from the Treatment Tip to the nsPEF subsystems and protective ground is reduced below 10 pF.

Figures 4A, 4B, 4C:
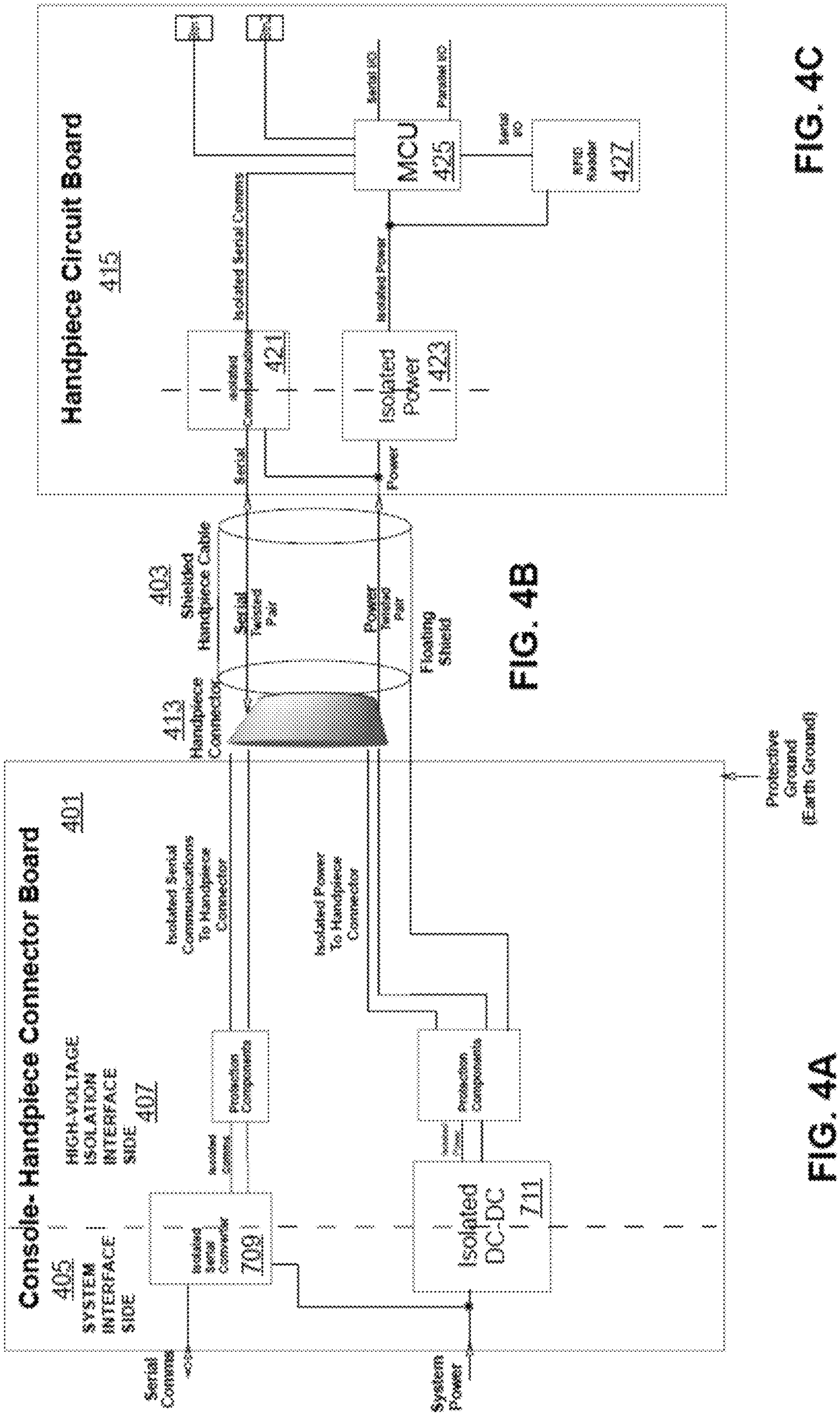
FIG. 4A is a schematic of one example of a console-handpiece isolation board as described herein. The dashed lines reflect a division between the system interface side and the connector side, which may be separated by the multi-functional isolation described herein.
FIG. 4B is a schematic of one example of a cable connecting a handpiece (applicator) to a console, as described herein.
FIG. 4C is a schematic of one example of a handpiece (handpiece circuit) as described herein.

FIG. 4A shows an example of a console-handpiece connection or isolation board 401, to which a handpiece cable 403 (shown schematically in FIG. 4B) may be attached to provide a multi-functional isolation as described herein. In FIG. 4A, the console-handpiece isolation board includes a system interface side 405 and a high-voltage isolation interface side 407. An isolated serial converter 709 and an isolated DC-DC component 711 may connect to a handpiece connector 413 for connecting to the handpiece cable 403 as shown in FIG. 4B. As shown in FIG. 4C, the handpiece cable 403 may then connect on the opposite end to a handpiece, including a handpiece circuit board 415. The connection to the cable at the handpiece may also be isolated by connecting to an isolated communications component 421 and an isolated power component 423. The handpiece circuit board 415 may include a variety of other components, such as a microprocessor (e.g., MCU 425) and RFID reader 427. In FIGS. 4A and 4C, the dashed lines reflect one example of a division in isolation regions (e.g., between a cable side and a handpiece side), which may be separated by multi-functional isolation as described herein. The RFID reader (or other sensor) may be used to detect the identity and/or connection with a treatment tip (see, e.g., FIG. 3).

Operation

The apparatuses described herein may be used to apply nanosecond/sub-nanosecond pulsed electrical fields to treat a patient. Any appropriate tissue may be treated. For example, the methods and apparatuses described herein may be used as part of any appropriate nanosecond (or sub-nanosecond) pulsed electrical therapy in which electrical energy is applied within the tissue (or in some cases on the tissue). For example, the method of applying energy described herein may be used to treat one or more of the following: organ tissue cancer (e.g., lung cancer, kidney cancer, pancreatic cancer, colon cancer, breast cancer, etc.), skin cancer, cherry angioma, warts, nevus, keloids/scars, aging skin, dermatological lesions, conditions and/or disease, molluscum angioma, necrobiosis lipoidica (NBL), melisma, lipoma epidermal/sebaceous cyst, basal cell carcinoma, any type of tumors or abnormal tissue growth (e.g., benign tumors, precancerous tumors). These methods may be methods of any other body tissue, including non-skin tissue (respiratory tissue, lung tissue, breast tissue, liver tissue, etc.).

To treat a patient, the handpiece may be prepared, e.g., by attaching or coupling an appropriate treatment tip, and the user may select or enter the treatment parameters (e.g., selecting the number of pulses, pulse duration, etc.) or a treatment protocol that specifies these parameters. The treatment tip may be applied to the tissue to be treated. The user may then trigger the start of the treatment, e.g., by pushing a switch, button, etc.

A typical treatment sequence may include two or more phases. Once the user triggers the start of treatment, the nsPEF system may starts an application placement check, followed by a treatment pulse sequence. The nsPEF system may first perform an applicator (such as a treatment apparatus or applicator) placement check (APC). This phase may be a lower-voltage pulse sequence, consisting of a small number (e.g., between about 1-50 pulses, e.g., about 5 to 20 pulses) having a fraction of the voltage to be applied for treatment (e.g., at between about 0.1% and about 20%, e.g., between about 0.5% and about 15%, between about 0.5% and 10%, etc.) of the treatment voltage, such as between about ~100V to 500V. These test pulses may be applied to determine if the system is in adequate communication with the tissue and is properly configured for nanosecond or sub-nanosecond, high voltage operation. Additional pulses can be delivered at this lower voltage if the APC "pass" criteria for stimulation is not met. This step may permit the apparatus to check that the treatment tip of the applicator is in sufficient contact with the tissue to begin a treatment pulse sequence. The APC phase may be subject to high and low tip-tissue impedance limits which must be met for several consecutive pulses before the apparatus will enter into the (high-voltage) treatment pulse sequence. There may also be a stability criteria that must be met, in which the tip-tissue impedance may be stable within a set percent limit to begin the treatment pulse sequence.

If the APC does not pass within a timeout limit, the user may be warned and the APC may start over again to ensure good tip-tissue contact. The APC parameters may be tailored for each tip type, lesion, and body location and these parameters may be stored in encrypted authenticated memory locations in the nsPEF System. APC pulses may be monitored and compared to limits which are also specific to the tip type, lesion, and body location. Once the APC is passed, the treatment pulse sequence can begin, to apply the treatment pulses, and the nsPEF System may output a Treatment Pulse Sequence.

A treatment pulse sequence may be, for example, a 1 kV to 18 kV (e.g., 1 kV to 15 kV) sequence of 10 to 300 pulses at a rate from 0.1 to 10 pulses per second. The treatment pulse sequence may be initiated within a few seconds (e.g., within 3 seconds, within 2 seconds, etc.) after the APC passes. This slight delay may allow time to charge the HV Marx capacitors to a higher voltage than required for lower-voltage APC pulses.

For each treatment pulse output by the nsPEF System, the digitizer and the RTC may ensure that the pulse conforms to strict limits for safety and efficacy, as detailed above for the RTC and digitizer. For example, two common issues that can occur during the application of treatment pulses are electrical arcs at the treatment tip or high tip-tissue impedance. Electrical arcs are not dangerous, but for each arc, the nsPEF system is not delivering the correct therapeutic voltage and an arc (particular type of high-current pulse) that are detected by the combination of the RTC and digitizer may cause the nsPEF system to pause pulsing, inform the user through a handpiece LED indicator and touchscreen message, and allow the user to reposition the handpiece to avoid the arc condition.

High tip-tissue impedance may result in a similar issue, which may not be safety-critical, but may be an indication that the treatment tip is not in sufficient contact with the tissue that a therapeutic pulse cannot be delivered. As in the arc situation above, the nsPEF system may pause pulsing, notify the user through the handpiece LEDs and/or touchscreen messages, and allow the user to correct the high tip-tissue impedance condition by improved positioning of the handpiece (e.g., treatment tip) on the treated tissue.

Embodiments of the methods of the present disclosure may be implemented using computer software, firmware or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

Certain embodiments may relate to a machine-readable medium (e.g., computer readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. It may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "mounted", "connected", "attached" or "coupled" to another feature or element, it can be directly mounted, connected, attached or coupled to the other feature or element or intervening features or elements may be present. In contrast, when a feature or element is referred to as being "directly mounted", "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present apparatuses and methods.

The terms "comprises" and/or "comprising," when used in this specification (including the claims), specify the presence of stated features, steps, operations, elements, and/or components, but do not preclude the presence or addition of one or more other features, steps, operations, elements, components, and/or groups thereof. Unless the context requires otherwise, "comprise", and variations such as "comprises" and "comprising," means various components can be co-jointly employed in the methods and articles (e.g., compositions and apparatuses including device and methods). For example, the term "comprising" will be understood to imply the inclusion of any stated elements or steps but not the exclusion of any other elements or steps.

Any of the apparatuses and methods described herein may include all or a sub-set of the components and/or steps, and these components or steps may be either non-exclusive (e.g., may include additional components and/or steps) or in some variations may be exclusive, and therefore may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the apparatuses and methods as it is set forth in the claims.

Various embodiments may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for delivering nanosecond pulsed electrical energy, the system comprising:

a console including:

a treatment controller, a nanosecond pulse generator configured to provide at least a high voltage pulsed output, and a console-handpiece isolation board comprising a high-voltage, low capacitance power supply isolator and one or more digital isolators; and a handpiece subsystem comprising:

a handpiece configured to deliver the high voltage pulsed output;

a low voltage control circuitry; and a handpiece cable coupled to the handpiece and coupled or configured to couple to the console-handpiece isolation board, wherein the console-handpiece isolation board couples the low voltage control circuitry across a multi-functional isolation barrier to the handpiece cable and wherein the high-voltage, low capacitance power supply isolator and the one or more digital isolators are configured to isolate low-voltage power and communication signals of the low voltage control circuitry from the high voltage pulsed output.

2. The system of claim 1, wherein the handpiece has a multi-functional isolation connection to the handpiece cable having a capacitance of 20 pF or less, so that a combination of the multi-functional isolation connection between the high voltage pulsed output and the handpiece cable with the multi-functional isolation connection between the handpiece and the handpiece cable limits a potential difference across a handpiece circuitry in the handpiece and electrically isolates handpiece power and communications from any other console subsystems when the nanosecond pulse generator delivers the high voltage pulsed output to the handpiece.

3. The system of claim 1, further comprising a multi-functional isolation connection has a capacitance of 20 pF or less.

4. The system of claim 1, wherein the handpiece cable is configured to electrically float.

5. The system of claim 4, wherein the handpiece cable comprises a shield, and wherein both the shield and conductive wires of the handpiece cable electrically float.

6. The system of claim 1, wherein the handpiece cable comprises a control line that is separate and electrically isolated from a power line.

7. The system of claim 1, wherein the handpiece comprises a handpiece circuit board having a microcontroller and a reader configured to receive information from a treatment tip on the handpiece.

8. The system of claim 1, wherein the handpiece comprises a microcontroller, a reader, and an encrypted authentication integrated circuit, further wherein the encrypted authentication integrated circuit is configured to ensure authenticity of the handpiece and/or a treatment tip coupled to the handpiece.

9. The system of claim 1, wherein the high voltage pulsed output generated by the nanosecond pulse generator is configured to have a voltage of greater than 5 kV and an output current of 300 A or greater.

10. The system of claim 1, wherein the nanosecond pulse generator is configured to provide at least a 10 kV/μs slew-rate, high voltage pulsed output.

11. The system of claim 1, wherein high voltage pulsed output generated by the nanosecond pulse generator comprises a voltage of greater than 1 kV.

12. The system of claim 1, further comprising a multi-functional isolation connection with the handpiece cable configured to limit a potential difference across a handpiece circuitry in the handpiece.

13. The system of claim 1, further comprising a separate control line configured to pass communication signals between the handpiece and the console wherein the separate control line is electrically isolated from a power line.

14. The system of claim 1, wherein the one or more digital isolators comprises a digital isolator configured to communicate modified control information from a pulse triggering and timing section to a high-voltage pulse output circuit section.

15. The system of claim 1, comprising a pulse triggering and timing section, wherein the pulse triggering and timing section is further configured to generate timing and triggering signals to drive one or more pulse transformers based on control information.

16. The system of claim 15, further comprising one or more low-leakage inductance pulse transformers in the pulse triggering and timing section, wherein the one or more low-leakage inductance pulse transformers in the pulse triggering and timing section are configured to drive a high-voltage switching circuits from the pulse triggering and timing section, wherein the low-leakage inductance pulse transformers provide low-capacitance isolation.

17. The system of claim 1, further comprising a system interconnect circuit section, wherein the system interconnect circuit section is configured to receive control information from a real-time controller.

18. The system of claim 1, wherein the nanosecond pulse generator is configured to provide pulses at a repetition rate in a range of 0.1 Hz to 10,000 Hz, and a pulse width of 0.1 ns to 1000 ns.

19. The system of claim 1, wherein the nanosecond pulse generator is configured to generate pulses with peak electric field strengths of at least 5 kV/cm.

20. The system of claim 1, wherein the handpiece cable comprises a high voltage cable configured to couple to a treatment applicator and a low voltage cable configured to couple to the low voltage control circuitry.

21. A system for delivering nanosecond pulsed electrical energy, the system comprising:

a console including:

a treatment controller, and a nanosecond pulse generator configured to provide at least a high voltage pulsed output;

a console-handpiece isolation board comprising a high-voltage, low capacitance power supply isolator and one or more digital isolators; and a handpiece subsystem comprising:

a handpiece configured to deliver the high voltage pulsed output; and a handpiece cable coupled to the handpiece and to the console-handpiece isolation board, wherein the high-voltage, low capacitance power supply isolator and the one or more digital isolators are configured to isolate the high voltage pulsed output from low-voltage power and communication signals while the high voltage pulse output of the nanosecond pulse generator is not isolated and is configured to directly pass to a patient.

* * * * *